United States Patent [19]

Capet et al.

[11] Patent Number: 5,686,622

[45] Date of Patent: Nov. 11, 1997

[54] THIAZOLIDINE DERIVATIVES, THEIR PREPARATION AND THE MEDICAMENTS CONTAINING THE SAME

[75] Inventors: Marc Capet, Thiais; Marie-Christine Dubroeucq, Enghein les Bains; Claude Guyon, Saint Maur des Fosses; Franco Manfre, Limeil-Brevannes, all of France

[73] Assignee: Rhone-Poulenc Rorer S.A., Antony, France

[21] Appl. No.: 750,867

[22] PCT Filed: Jun. 19, 1995

[86] PCT No.: PCT/FR95/00808

§ 371 Date: Dec. 19, 1996

§ 102(e) Date: Dec. 19, 1996

[87] PCT Pub. No.: WO95/35314

PCT Pub. Date: Dec. 28, 1995

[30] Foreign Application Priority Data

Jun. 22, 1994 [FR] France ................................... 94 07627

[51] Int. Cl.$^6$ ................................................ C07K 5/062
[52] U.S. Cl. ........................................ 548/201; 548/200
[58] Field of Search ................................... 548/200, 201

[56] References Cited

FOREIGN PATENT DOCUMENTS

| 0527069 | 2/1993 | European Pat. Off. |
| WO94/15914 | 7/1994 | WIPO |
| WO94/15915 | 7/1994 | WIPO |
| WO94/15954 | 7/1994 | WIPO |
| WO94/15955 | 7/1994 | WIPO |

OTHER PUBLICATIONS

Derwent Abstract of EP A 0527069. (1992).

*Primary Examiner*—Robert Gerstl
*Attorney, Agent, or Firm*—Finnegan, Henderson, Farabow, Garrett & Dunner, L.L.P.

[57] ABSTRACT

Thiazolidine derivatives of formula (I), in which $R_1$, $R_2$, $R_3$, $R_4$ and $R_5$ are as defined in the specification. The invention also concerns the salts of these derivatives, the preparation thereof and drugs containing same.

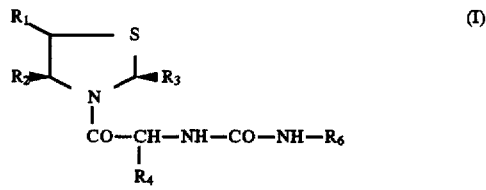

12 Claims, No Drawings

THIAZOLIDINE DERIVATIVES, THEIR PREPARATION AND THE MEDICAMENTS CONTAINING THE SAME

The present invention relates to thiazolidine derivatives of formula:

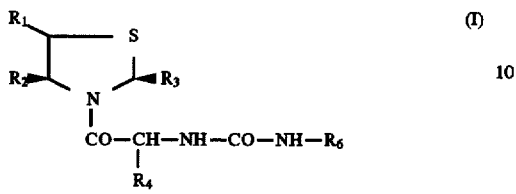

to their salts, to their preparation and to the medicaments containing them.

In formula (I),

R$_1$ represents a radical —(CH$_2$)$_n$—COORa or —(CH$_2$)$_n$—CONRbRc,

R$_2$ represents a phenyl radical optionally substituted with one or more substituents chosen from halogen atoms and alkyl, alkoxy, hydroxyl, nitro, amino, monoalkylamino, dialkylamino, alkoxycarbonyl, trifluoromethyl and trifluoromethoxy radicals, R$_3$ represents a radical —COORd or —CONReRf, R$_4$ represents a hydrogen atom or an alkyl radical, R$_5$ represents a phenyl radical optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—SO$_3$H (in salt form), —CH=CH—alk', —C(=NOH)—COOX, —S—alk—COOX, —SO—alk—COOX, —SO$_2$—alk—COOX, —O—CH$_2$—alk'—COOX, —CX=N—O—alk—COOX, —alk—N(OH)—CO—alk, —alk—SO$_2$H, —SO$_2$—NH—CO—Rg, —SO$_2$—NH—SO$_2$—Rg, —CO—NH—CO—Rg, —CO—NH—SO$_2$—Rg, —B(OH)$_2$, —C(NH$_2$)=NOH, —SO$_2$—NH—Rh, —CO—NH—Rh,

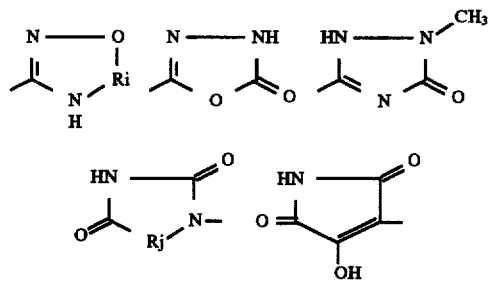

and 2,2-dimethyl-4,6-dioxo-1,3-dioxan-5-yl radicals,

Ra represents a hydrogen atom or an alkyl radical,

Rb represents a hydrogen atom or an alkyl radical,

Rc represents an alkyl or 5-tetrazolyl radical, a phenylalkyl radical in which the phenyl ring is optionally substituted with one or more substituents chosen from halogen atoms and alkyl, alkoxy and alkylthio radicals or a phenyl radical optionally substituted with one or more substituents chosen from halogen atoms and alkyl, alkoxy and alkylthio radicals, or alternatively Rb and Rc form, with the nitrogen atom to which they are attached, a saturated or unsaturated mono- or polycyclic heterocycle containing 4 to 9 carbon atoms and one or more hetero atoms chosen from oxygen, nitrogen and sulphur and optionally substituted with one or more alkyl radicals, Rd represents an alkyl radical, Re represents a hydrogen atom or an alkyl radical, Rf represents an alkyl, cycloalkyl or cycloalkylalkyl radical, or alternatively Re and Rf form, with the nitrogen atom to which they are attached, a saturated or unsaturated mono- or polycyclic heterocycle containing 4 to 9 carbon atoms and one or more hetero atoms chosen from oxygen, nitrogen and sulphur and optionally substituted with one or more alkyl radicals, Rg represents an alkyl, cycloalkyl or trifluoromethyl radical, or a phenyl radical optionally substituted with one or more substituents chosen from cyano, alkoxy, nitro and amino radicals and halogen atoms, Rh represents a 5-tetrazolyl radical, Ri represents C=O or S=O, Rj represents O or C=O, n is equal to 0 or 1, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical.

In the above definitions or in those which will be mentioned below, except where otherwise mentioned, the alkyl, alkylene and alkoxy radicals and portions contain 1 to 4 carbon atoms in a straight or branched chain and the cycloalkyl radicals or portions contain 3 to 6 carbon atoms.

The compounds of formula (I) have isomeric forms. These isomers also form part of the invention.

When Rb and Rc or Re and Rf form, with the nitrogen atom to which they are attached, a saturated or unsaturated mono- or polycyclic heterocycle containing 4 to 9 carbon atoms and one or more hetero atoms chosen from oxygen, nitrogen and sulphur and optionally substituted with one or more alkyl radicals, this heterocycle is preferably a morpholinyl or thiomorpholinyl residue, a piperidyl residue optionally substituted with one or more alkyl radicals, or a pyrrolidinyl, 1,2,3,4-tetrahydroquinolyl or N-alkylpiperazinyl residue.

The compounds of formula (I) for which R$_1$ represents a radical —(CH$_2$)n—COORa, n is equal to 0 or 1, Ra represents an alkyl radical and R$_5$ represents a phenyl radical optionally substituted with one or more substituents chosen from halogen atoms and alkyl, alkoxy, alkylthio, trifluoromethyl, alkoxycarbonyl, nitro, acyl, cyano, sulphamoyl, carbamoyl, alkoxyiminoalkyl, alkoxyaminocarbonyl, trifluoromethylsulphonamido, —alk—O—CO—alk, —alk—COOX, —alk—O—alk, —alk'—COOX, —O—alk—COOX, —CH=CH—COOX, —CO—COOX, —alk—SO$_3$H (in salt form), —CH=CH—alk', —S—alk—COOX, —SO—alk—COOX, —SO$_2$—alk—COOX, —O—CH$_2$—alk'—COOX or —CX=N—O—alk—COOX radicals in which X is an alkyl or phenylalkyl radical may be prepared by the action of a derivative of formula:

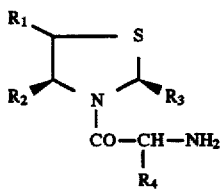

in which $R_1$ represents a radical —$(CH_2)_n$—COORa, n is equal to 0 or 1, Ra represents an alkyl radical, and $R_2$, $R_3$ and $R_4$ have the same meanings as in formula (I), on a phenyl isocyanate in which the phenyl ring is optionally substituted with one or more substituents chosen from halogen atoms and alkyl, alkoxy, alkylthio, trifluoromethyl, alkoxycarbonyl, nitro, acyl, cyano, sulphamoyl, carbamoyl, alkoxyiminoalkyl, alkoxyaminocarbonyl, trifluoromethylsulphonamido, —alk—O—CO—alk, —alk—COOX, —alk—O—alk, —alk'—COOX, —O—alk—COOX, —CH=CH—COOX, —CO—COOX, —alk—SO$_3$H (in salt form), —CH=CH—alk', —S—alk—COOX, —SO—alk—COOX, —SO$_2$—alk—COOX, —O—CH$_2$—alk'—COOX or —CX=N—O—alk—COOX radicals in which X is an alkyl or phenylalkyl radical, alk represents an alkyl or alkylene radical, and alk' represents a hydroxyalkyl, hydroxyalkylene, alkoxyalkyl or alkoxyalkylene radical.

This reaction is generally carried out in an inert solvent such as tetrahydrofuran, dimethylformamide, a chlorinated solvent (chloroform or 1,2-dichloroethane for example) or an aromatic solvent (benzene or toluene for example), at a temperature between 10° C. and the boiling point of the reaction medium.

The phenyl isocyanates are commercially available or may be obtained by application or adaptation of the methods described by R. Richter et al., The Chemistry of Cyanate and their Thio Derivatives, S. Patai, part 2, Wiley New York (1977) and in the examples.

The derivatives of formula (II) may be obtained by the action of a derivative of formula:

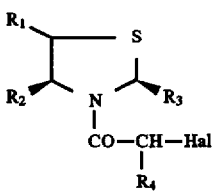

in which $R_1$ represents a radical —$(CH_2)_n$—COORa, n is equal to 0 or 1, Ra represents an alkyl radical, $R_2$, $R_3$ and $R_4$ have the same meanings as in formula (I) and Hal represents a halogen atom (preferably chlorine or bromine), on sodium azide in order to form the corresponding azido product, which is then reacted with triphenylphosphine and then water in order to hydrolyse the iminophosphorane.

The reaction with sodium azide is generally carried out in an inert solvent such as dimethylformamide, at a temperature in the region of 20° C. The reaction with triphenylphosphine is preferably carried out in an inert solvent such as tetrahydrofuran, at a temperature in the region of 20° C.

The derivatives of formula (III) may be obtained by the action of a derivative of formula:

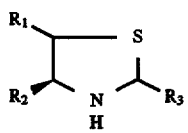

in which $R_1$ represents a radical —$(CH_2)_n$—COORa, n is equal to 0 or 1, Ra represents an alkyl radical, and $R_2$ and $R_3$ have the same meanings as in formula (I), on a derivative of formula:

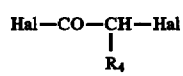

in which Hal represents a halogen atom (preferably chlorine or bromine) and $R_4$ has the same meanings as in formula (I).

This reaction is preferably carried out in an aromatic solvent such as toluene, in the presence of an organic or inorganic base such as a trialkylamine (triethylamine for example) or sodium hydrogen carbonate, at the boiling point of the reaction medium.

The derivatives of formula (V) are commercially available or may be prepared from the corresponding acid, which is converted into the acid chloride by any method known to those skilled in the art, and especially using oxalyl chloride or thionyl chloride.

The derivatives of formula (IV) for which $R_1$ represents a radical —$(CH_2)_n$—COORa, n is equal to 0, Ra represents an alkyl radical, $R_3$ represents a radical —COORd and Rd represents an alkyl radical, may be obtained by the action of a derivative of formula:

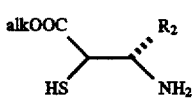

in which $R_2$ has the same meanings as in formula (I) and alk represents an alkyl radical, on an alkyl 2,2-dimorpholinoacetate.

This reaction is generally carried out in an inert solvent such as an alcohol (methanol for example), in the presence of a trialkylamine such as triethylamine, at the boiling point of the reaction medium.

The alkyl 2,2-dimorpholinoacetates may be obtained by application or adaptation of the method described by R. Heymes et al., Bull. Soc. Chim., 2343-9 (1973).

The derivatives of formula (VI) may be obtained by the action of sodium methoxide on a derivative of formula:

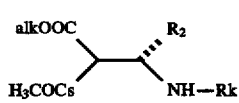

in which $R_2$ has the same meanings as in formula (I), alk represents an alkyl radical and Rk represents a protecting group for the amine function such as tert-butoxycarbonyl (Boc), followed by deprotection of the amine function.

The action of sodium methoxide is preferably carried out in methanol, at a temperature in the region of 20° C., and the deprotection is carried out using an inorganic acid such as hydrochloric acid, at a temperature in the region of 20° C.

The derivatives of formula (VII) may be obtained by the action of potassium thioacetate on a derivative of formula:

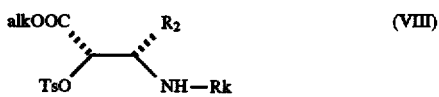

in which $R_2$ has the same meanings as in formula (I), Rk represents a protecting group for the amine function such as tert-butoxycarbonyl (Boc), alkyl represents an alkyl radical and Ts represents a tosyl residue.

This reaction is preferably carried out in an inert solvent such as acetone, at the boiling point of the reaction medium.

The derivatives of formula (VIII) may be obtained by tosylation of the derivatives of formula:

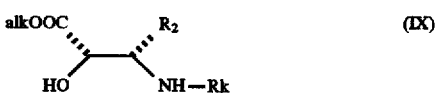

in which $R_2$ has the same meanings as in formula (I), Rk represents a protecting group for the amine function such as tert-butoxycarbonyl (Boc) and alk represents an alkyl radical.

This reaction is carried out using tosyl chloride, in an inert solvent such as dichloromethane, in the presence of a trialkylamine such as triethylamine, at a temperature in the region of 20° C., or in pyridine, at a temperature between 0° and 25° C.

The derivatives of formula (IX) may be prepared by application or adaptation of the method described in patent WO 93/17997.

The derivatives of formula (IV) for which $R_1$ represents a radical —$(CH_2)_n$—COORa, n is equal to 1, Ra represents an alkyl radical, $R_3$ represents a radical —COORd and Rd represents an alkyl radical, may be obtained by alcoholysis of a derivative of formula:

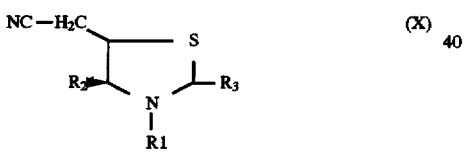

in which $R_2$ has the same meanings as in formula (I), $R_3$ represents a radical —COORd, Rd represents an alkyl radical and R1 represents a protecting group such as benzyloxycarbonyl, followed by deprotection of the amine function.

This alcoholysis is generally carried out in an acidic medium (hydrochloric acid for example), using an alcohol (1–4 C in a straight or branched chain), at a temperature between 20° C. and the boiling point of the reaction medium. The deprotection is preferably carried out either using iodotrimethylsilane, in an inert solvent (chloroform for example), at a temperature between 20° C. and the boiling point of the reaction medium, or by hydrogenolysis using hydrogen, in the presence of a hydrogenation catalyst such as palladium-on-charcoal, at a temperature between 20° C. and the boiling point of the reaction medium, or using ammonium formate in the presence of palladium, in an alcohol such as methanol, at the boiling point of the reaction medium.

The derivatives of formula (X) may be obtained by the action of an alkali metal cyanide on a derivative of formula:

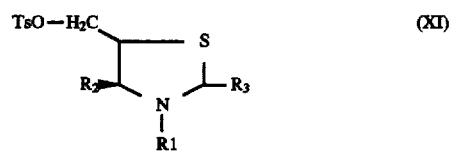

in which $R_2$ has the same meanings as in formula (I), $R_3$ represents a radical —COORd, Rd represents an alkyl radical, R1 represents a protecting group such as benzyloxycarbonyl and Ts represents a tosyl residue.

This reaction is carried out in an inert solvent such as dimethylformamide, tetrahydrofuran or an alcohol (methanol for example), at a temperature between 20° C. and 100° C.

The derivatives of formula (XI) may be obtained by tosylation of the derivative of formula:

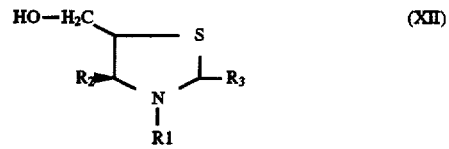

in which $R_2$ has the same meanings as in formula (I), $R_3$ represents a radical —COORd, Rd represents an alkyl radical and R1 represents a protecting group such as benzyloxycarbonyl.

This reaction is generally carried out using tosyl chloride, in an inert solvent such as dichloromethane, in the presence of a trialkylamine such as triethylamine, at a temperature in the region of 20° C., or in pyridine, at a temperature between 0° and 25° C.

The derivatives of formula (XII) may be obtained by the action of sodium borohydride on a derivative of formula:

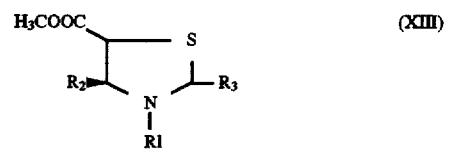

in which $R_2$ has the same meanings as in formula (I), $R_3$ represents a radical —COORd, Rd represents an alkyl radical and R1 represents a protecting group such as benzyloxycarbonyl.

This reaction is carried out in an alcohol such as methanol, at a temperature between 20° C. and the boiling point of the reaction medium.

The derivatives of formula (XIII) may be obtained by protection of the amine function of a corresponding derivative of formula (IV) for which $R_1$ represents a radical —$(CH_2)_n$—COORa, n is equal to 0, Ra represents an alkyl (1 C) radical, $R_2$ has the same meanings as in formula (I), $R_3$ represents a radical —COORd and Rd represents an alkyl radical, using a protecting agent such as benzyl chloroformate.

This reaction is carried out in an inert solvent such as a chlorinated solvent (dichloromethane for example), in the presence of a trialkylamine (triethylamine for example), at a temperature in the region of 20° C.

The derivatives of formula (IV) for which $R_1$ represents a radical —$(CH_2)_n$—COORa, n is equal to 0 or 1, Ra represents an alkyl radical, $R_3$ represents a radical —CONReRf, and $R_2$, Re and Rf have the same meanings as in formula (I), may be obtained by the action of an amine of formula HNReRf in which Re and Rf have the same meanings as in formula (I), on an acid of formula:

(XIV)

$$\text{structure with } R_1, R_2, S, N-R_m, \text{COOH}$$

in which $R_1$ represents a radical —$(CH_2)_n$—COORa, n is equal to 0 or 1, Ra represents an alkyl radical, $R_2$ has the same meanings as in formula (I) and Rm represents a methoxycarbonyl or (9-fluorenylmethyl)oxycarbonyl (Fmoc) radical, followed by deprotection of the amine function.

This reaction is carried out in the presence of a peptide coupling agent such as a carbodiimide (N,N'-dicyclohexylcarbodiimide for example) or N,N'-carbonyldiimidazole, in an inert solvent such as an ether (tetrahydrofuran or dioxane for example), an amide (dimethylformamide for example) or a chlorinated solvent (methylene chloride or chloroform for example), at a temperature between 0° C. and the boiling point of the reaction medium. Deprotection of the amine function is carried out by any known method which does not affect the other functions in the product; in particular, in the case where Rm represents a methoxycarbonyl, the process is performed using iodotrimethylsilane, in an inert solvent such as chloroform, at a temperature between 20° C. and the boiling point of the reaction medium, and in the case where Rm represents a (9-fluorenylmethyl)oxycarbonyl radical, the process is performed using a base such as piperidine, morpholine or ethanolamine, in an inert solvent such as dimethylformamide or dichloromethane, at a temperature in the region of 20° C.

The derivatives of formula (XIV) may be obtained by hydrolysis of a derivative of formula:

(XV)

$$\text{structure with } R_1, R_2, S, N-R_m, R_3$$

in which $R_1$ represents a radical —$(CH_2)_n$—COORa, n is equal to 0 or 1, Ra represents an alkyl radical, $R_2$ has the same meanings as in formula (I), $R_3$ represents a tert-butoxycarbonyl radical and Rm represents a methoxycarbonyl or (9-fluorenylmethyl)oxycarbonyl (Fmoc) radical.

This reaction is generally carried out using iodotrimethylsilane, in an inert solvent such as a chlorinated solvent (chloroform for example), at a temperature in the region of 25° C.

The derivatives of formula (XV) may be obtained by the action of a chloride Cl-Rm in which Rm represents a methoxycarbonyl or (9-fluorenylmethyl)oxycarbonyl radical on a corresponding derivative of formula (IV) for which $R_1$ represents a radical —$(CH_2)_n$—COORa, n is equal to 0 or 1, Ra represents an alkyl radical, $R_2$ has the same meanings as in formula (I) and $R_3$ represents a tert-butoxycarbonyl radical.

This reaction is generally carried out in an inert solvent such as a chlorinated solvent (dichloromethane for example), in the presence of a trialkylamine (triethylamine for example), at a temperature in the region of 25° C.

The compounds of formula (I) for which $R_1$ represents a radical —$(CH_2)_n$—COORa, n is equal to 0 or 1 and Ra is an alkyl radical, may also be prepared by the action of a reactive derivative of carbamic acid, optionally obtained in situ by the action of a reactive derivative of carbonic acid chosen from N,N'-carbonyldiimidazole, phosgene, diphosgene, triphosgene and p-nitrophenyl chloroformate on a derivative of formula (II) for which $R_1$ represents a radical —$(CH_2)$n—COORa, Ra represents an alkyl radical, and $R_2$, $R_3$ and $R_4$ have the same meanings as in formula (I), on an aniline in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—SO₃H (in salt form), —CH=CH—alk', —C(=NOH)—COOX, —S—alk—COOX, —SO—alk—COOX, —SO₂—alk—COOX, —O—CH₂—alk'—COOX, —CX=N—O—alk—COOX, —alk—N(OH)—CO—alk, —alk—SO₂H, —SO₂—NH—CO—Rg, —SO₂—NH—SO₂—Rg, —CO—NH—CO—Rg, —CO—NH—SO₂—Rg, —B(OH)₂, —C(NH₂)=NOH, —SO₂—NH—R$_h$, —CO—NH—R$_h$, $$\text{structures showing various ring systems with N, O, NH, HN, CH}_3, R_i, R_j$$

and 2,2-dimethyl-4,6-dioxo-1,3-dioxan-5-yl radicals, Ri represents C=O or S=O, Rj represents O or C=O, n is equal to 0 or 1, X represents a hydrogen atom or an alkyl or phenylalkyl radical, alk represents an alkyl or alkylene radical and alk' represents a hydroxyalkyl, hydroxyalkylene, alkoxyalkyl or alkoxyalkylene radical.

This reaction is generally carried out in an inert solvent such as tetrahydrofuran, dimethylformamide, a chlorinated solvent (chloroform or 1,2-dichloroethane for example) or an aromatic solvent (benzene or toluene for example), at a temperature between 20° C. and the boiling point of the solvent.

The reactive derivative of carbamic acid may be obtained under the same temperature and solvent conditions.

The optionally substituted anilines are commercially available or may be obtained by application or adaptation of the methods described by R. Schröter, Methoden der organischen Chemie, Houben Weil, Band XI/1, p. 360; G. J. Esselen et al., J. Am. Chem. Soc., 36, 322 (1914); G. Adriant et al., Bull. Soc. Chim. Fr, 1511 (1970); W. A. Jacobs et al., J. Am. Chem. Soc., 39, 2438 (1917) and J. Am. Chem. Soc., 39, 1438 (1917).

The compounds of formula (I) for which $R_1$ represents a radical —$(CH_2)_n$—CONRbRc may be prepared by the action of a corresponding compound of formula (I), for which $R_1$ represents a radical —$(CH_2)_n$—COORa, n is equal to 0 or 1 and Ra represents a hydrogen atom, on an amine of formula HNRbRc in which Rb and Rc have the same meanings as in formula (I).

This reaction is generally carried out in the presence of a coupling agent used in peptide chemistry, such as a carbodiimide (for example N,N'-dicyclohexylcarbodiimide) or N,N'-carbonyldiimidazole, in an inert solvent such as an ether (tetrahydrofuran or dioxane for example), an amide (N,N-dimethylformamide) or a chlorinated solvent (methylene chloride, 1,2-dichloroethane or chloroform for example), at a temperature between 0° C. and the reflux temperature of the reaction mixture.

The compounds of formula (I) for which $R_1$ represents a radical —$(CH_2)_n$—COORa, n is equal to 0 or 1 and Ra represents a hydrogen atom, may be prepared by hydrolysis of the corresponding compounds of formula (I) for which $R_1$ represents a radical —$(CH_2)_n$—COORa for which n is equal to 0 or 1 and Ra represents an alkyl radical.

This reaction is generally carried out in an inert solvent such as water, tetrahydrofuran or a mixture of these solvents, in the presence of an alkali metal hydroxide such as sodium hydroxide, at a temperature between 0° and 25° C.

The compounds of formula (I) for which $R_5$ represents a phenyl radical substituted with a radical containing a residue COOX in which X represents a hydrogen atom may also be prepared by hydrogenolysis of the corresponding benzyl esters.

This reaction is generally carried out in an inert solvent such as an alcohol (methanol for example), using hydrogen or ammonium formate, in the presence of a hydrogenation catalyst such as palladium-on-charcoal, at a temperature between 20° C. and the boiling point of the reaction medium.

It is understood by those skilled in the art that, in order to carry out the processes according to the invention which are described above, it may be necessary, in order to avoid side reactions, to introduce protecting groups for the amine, alcohol, acid and ketone functions such as those described by T. W. Greene, "Protective Groups in Organic Synthesis", John Wiley and Sons, New York. For example, the amine functions may be blocked in the form of tert-butyl or methyl carbamates, and then regenerated using iodotrimethylsilane, in the form of 9-fluorenylmethyl carbamate and then regenerated using a base such as piperidine or morpholine, or in the form of benzyl carbamates and then regenerated by hydrogenation after the process according to the invention has been carried out. The alcohol functions may, for example, be blocked in the form of benzoate and then regenerated by hydrolysis in an alkaline medium after the process according to the invention has been carried out. The ketone functions may be blocked in the form of 1,3-dioxolane and then regenerated using a hydrochloric acid-acetic acid mixture.

The enantiomers of the compounds of formula (I) may be obtained by resolution of the racemic mixtures, for example by chromatography on a chiral column or by synthesis from chiral precursors.

The compounds of formula (I) may be purified by the usual known methods, for example by crystallization, chromatography or extractions.

The compounds of formula (I) containing a basic residue may optionally be converted into addition salts with an inorganic or organic acid by the action of such an acid in an organic solvent such as an alcohol, a ketone, an ether or a chlorinated solvent.

The compounds of formula (I) containing an acidic residue may optionally be converted into metal salts or into addition salts with nitrogen-containing bases according to methods that are known per se. These salts may be obtained by the action of a metal base (an alkali metal or alkaline-earth metal base for example), ammonia, an amine or an amine salt on a compound of formula (I), in a solvent. The salt formed is isolated by the usual methods.

These salts also form part of the invention.

Examples of pharmaceutically acceptable salts which may be mentioned are the addition salts with inorganic or organic acids (such as acetate, propionate, succinate, benzoate, fumarate, maleate, oxalate, methanesulphonate, isethionate, theophyllineacetate, salicylate, methylenebis-β-oxynaphthoate, hydrochloride, sulphate, nitrate and phosphate), the salts with alkali metals (sodium, potassium and lithium) or with alkaline-earth metals (calcium and magnesium), the ammonium salt, and the salts of nitrogen-containing bases (ethanolamine, trimethylamine, methylamine, benzylamine, N-benzyl-β-phenethylamine, choline, arginine, leucine, lysine and N-methylglucamine).

The compounds of formula (I) exhibit advantageous pharmacological properties. These compounds have a strong affinity for the cholecystokinin (CCK) and gastrin receptors and are thus useful in the treatment and prevention of disorders linked to CCK and to gastrin in the nervous system and in the gastrointestinal system, Thus, these compounds may be used for the treatment or prevention of psychoses, anxiety disorders, depression, neurodegeneration, panic attacks, Parkinson's disease, tardive dyskinesia, irritable bowel syndrome, acute pancreatitis, ulcers, intestinal motility disorders and certain CCK-sensitive tumours, as appetite regulators, in withdrawal from chronic treatments and alcohol or drug abuse, and as constrictors of the pupil of the eye.

These compounds also have a potentiating effect on the analgesic activity of narcotic and non-narcotic drugs. In addition, they may have an intrinsic analgesic effect.

Moreover, the compounds having a strong affinity for the CCK receptors modify the capacities for memorization. Consequently, these compounds may be effective in memory disorders.

The affinity of the compounds of formula (I) for the CCK receptors was determined according to a technique based on that of A. Saito et al., (J. Neuro. Chem., 37, 483–490 (1981)) in the cerebral cortex and in the pancreas.

In these tests, the $IC_{50}$ of the compounds of formula (I) is generally less than or equal to 1000 nM.

Moreover, it is known that the products which recognize the CCK central receptors have a similar specificity for the gastrin receptors in the gastrointestinal tract (Bock et al., J. Med. Chem., 32, 16–23 (1989); Reyfeld et al., Am. J. Physiol., 240, G255–266 (1981); Beinfeld et al., Neuropeptides, 3, 411–427 (1983).

The compounds of formula (I) are of low toxicity. Their $LD_{50}$ is generally greater than 40 mg/kg via the subcutaneous route in mice.

The compounds of particular interest are those of formula (I) for which $R_1$ represents a radical —$(CH_2)_n$—COORa or —$(CH_2)_n$—CONRbRc, $R_2$ represents a phenyl radical optionally substituted with one or more substituents chosen from halogen atoms and alkyl, alkoxy, hydroxyl, alkoxycarbonyl, trifluoromethyl and trifluoromethoxy radicals, $R_3$ represents a radical —COORd or —CONReRf, $R_4$ represents a hydrogen atom or an alkyl (1 or 2 C) radical, $R_5$ represents a phenyl radical optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—SO$_3$H (in salt form), —CH=CH—alk', —C(=NOH)—COOX, —S—alk—COOX, —SO—alk—COOX, —SO$_2$—alk—COOX, —O—CH$_2$—alk'—COOX, —CX=N—O—alk—COOX, —alk—N(OH)—CO—alk and —alk-SO$_2$H, Ra represents a hydrogen atom or an alkyl radical Rb represents a hydrogen atom or an alkyl radical, Rc represents an alkyl or 5-tetrazolyl radical, a phenylalkyl radical in which the phenyl ring is optionally substituted with one or more substituents chosen from halogen atoms and alkyl, alkoxy and alkylthio radicals or a phenyl radical optionally substituted with one or more substituents chosen from halogen atoms and alkyl, alkoxy and alkylthio radicals, or alternatively Rb and Rc form, with the nitrogen atom to which they are attached, a saturated or unsaturated mono- or polycyclic heterocycle containing 4 to 9 carbon atoms and one or more hetero atoms chosen from oxygen, nitrogen and sulphur and optionally substituted with one or more alkyl radicals, Rd represents an alkyl radical, Re represents a hydrogen atom or an alkyl radical, Rf represents an alkyl, cycloalkyl or cycloalkylalkyl radical, or alternatively Re and Rf form, with the nitrogen atom to which they are attached, a saturated or unsaturated mono- or polycyclic heterocycle containing 4 to 9 carbon atoms and one or more hetero atoms chosen from oxygen, nitrogen and sulphur and optionally substituted with one or more alkyl radicals, n is equal to 0 or 1

X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, the isomers thereof and the salts thereof.

Among these compounds, the following are preferred:

tert-butyl (2S,4S,5R)-5-methoxycarbonyl-3-{2-[3-(3-methylphenyl)ureido]acetyl}-4-phenyl-2-thiazolidinecarboxylate, 3-{3-[2-(2S,4S,5R)-2-tert-butoxycarbonyl-5-carboxy-4-phenyl-3-thiazolidinyl)-2-oxoethyl]ureido}phenylacetic acid, (S)-2-{3-{3-[2-((2S,4S,5R)-2-tert-butoxycarbonyl-5-carboxy-4-phenyl-3-thiazolidinyl)-2-oxoethyl]ureido}phenyl}propionic acid, tert-butyl (2S,4S,5R)-5-methoxycarbonyl-3-{2-[3-(3-methylphenyl)ureido]acetyl}-4-(2-fluorophenyl)-2-thiazolidinecarboxylate, (2S,4S,5R)-2-tert-butoxycarbonyl-3-{2-[3-(3-methylphenyl)ureido]acetyl}-4-(2-fluorophenyl)-5-thiazolidinecarboxylic acid, and the salts thereof.

The examples which follow illustrate the invention.

EXAMPLE 1

50 µl of 3-methylphenyl isocyanate are added to a round-bottomed flask containing 0.14 g of tert-butyl (2S,4S,5R)-3-(2-aminoacetyl)-5-methoxycarbonyl-4-phenyl-2-thiazolidinecarboxylate dissolved in 10 ml of tetrahydrofuran. The reaction mixture is stirred for 12 hours at a temperature in the region of 25° C. and then concentrated to dryness under reduced pressure at 35° C. The crude product is purified by chromatography on silica [eluent: ethyl acetate/cyclohexane (40/60 by volume)]. The fractions containing the expected product are combined and concentrated to dryness under reduced pressure at 40° C. 0.13 g of tert-butyl (2S,4S,5R)-5-methoxycarbonyl-3-{2-[3-(3-methylphenyl)ureido]acetyl}-4-phenyl-2-thiazolidinecarboxylate is thus obtained in the form of a white foam, $[\alpha]_D^{25}=-9.5°\pm0.8°$ (c=1.0; CH$_3$OH), $^1$H NMR: (200 MHz, (CD$_3$)$_2$SO with addition of a few drops of CD$_3$COOD, at a temperature of 373 K, δ in ppm): 1.51 (s, 9H: CH$_3$ of the tert-butyl); 2.28 (s, 3H: ArCH$_3$); 3.69 and 4.05 (broad d and d respectively, J=17 Hz, 1H each: COCH$_2$N); 3.78 (s, 3H: COOCH$_3$); 4.31 (d, J=3.5 Hz, 1H: at C5 of the ring); 5.75 (s, 1H: H at C2 of the ring); 5.86 (d, J=3.5 Hz, 1H: H at C4 of the ring); 6.76 (broad d, J=7.5 Hz, 1H: aromatic H (H ortho to the CH$_3$)); 7.10 (t, J=7.5 Hz, 1H: aromatic H (H meta to the CH$_3$) ); from 7.10 to 7.50 (mt, 5H: aromatic H); 7.73 (mt, 2H: H ortho to the phenyl).

A. tert-Butyl (2S,4S,5R)-3-(2-aminoacetyl)-5-methoxycarbonyl-4-phenyl-2-thiazolidinecarboxylate may be prepared in the following way: to a solution of 0.42 g of tert-butyl (2S,4S,5R)-3-(2-azidoacetyl)-5-methoxycarbonyl-4-phenyl-2-thiazolidinecarboxylate in 10 ml of tetrahydrofuran is added, at a temperature in the region of 25° C., 0.27 g of triphenylphosphine. The reaction mixture is stirred for 15 minutes at a temperature in the region of 25° C., then 20 µl of water are added, the stirring is continued for 12 hours at a temperature in the region of 25° C. and the mixture is concentrated to dryness under reduced pressure at 35° C. The residue obtained is diluted with 20 ml of diethyl ether and extracted with 10 ml of aqueous 0.1N hydrochloric acid solution. The aqueous phase is separated out after settling of the phases has taken place, brought to pH 9 by addition of aqueous 1N sodium hydroxide solution and extracted with 3 times 20 ml of diethyl ether. The combined organic phases are washed with 20 ml of water, dried over magnesium sulphate and concentrated to dryness under reduced pressure at 40° C. 0.14 g of tert-butyl (4S)-3-(2-aminoacetyl)-5-methoxycarbonyl-4-phenyl-2-thiazolidinecarboxylate, as a mixture of the isomers at positions 2 and 5, is thus obtained in the form of a yellow oil which is used without further purification in the subsequent syntheses.

B. tert-Butyl (2S,4S,5R)-3-(2-azidoacetyl)-5-methoxycarbonyl-4-phenyl-2-thiazolidinecarboxylate may be prepared in the following way: to a solution of 0.46 g of tert-butyl (2S,4S,5R)-3-(2-bromoacetyl)-5-methoxycarbonyl-4-phenyl-2-thiazolidinecarboxylate in 5 ml of dimethylformamide is added, at a temperature in the region of 20° C., a solution of 0.07 g of sodium azide in 5 ml of dimethylformamide. The reaction medium is stirred for 1 hour at this temperature and then hydrolysed by addition of 15 ml of water and extracted with twice 20 ml of diethyl ether. The combined organic phases are washed with twice 20 ml of water, dried over magnesium sulphate and concentrated to dryness under reduced pressure at 25° C. 0.5 g of tert-butyl (2S,4S,5R)-3-(2-azidoacetyl)-5-methoxycarbonyl-4-phenyl-2-thiazolidinecarboxylate is thus obtained in the form of a yellow oil, which is used without further purification in the subsequent syntheses.

C. tert-Butyl (2S,4S,5R)-3-(2-bromoacetyl)-5-methoxycarbonyl-4-phenyl-2-thiazolidinecarboxylate may be prepared in the following way: to a mixture containing 0.86 g of tert-butyl (4S)-5-methoxycarbonyl-4-phenyl-2-thiazolidinecarboxylate as a mixture of the isomers at positions 2 and 5, and 0.22 g of sodium hydrogen carbonate in 15 ml of toluene is added a solution of 0.54 g of bromoacetyl bromide in 5 ml of toluene. The reaction medium is heated at reflux for 1.5 hour then, after cooling to a temperature in the region of 20° C., diluted with 40 ml of ethyl acetate, washed successively with 20 ml of saturated aqueous sodium hydrogen carbonate solution and with 20 ml of water, dried over magnesium sulphate and concentrated to dryness under reduced pressure at 40° C. The crude product is purified by chromatography on silica [eluent: cyclohexane/ethyl acetate (90/10 and then 80/20 by volume)]. The fractions containing the product are combined and concentrated to dryness under reduced pressure at 30° C. 0.19 g of tert-butyl (2S,4S,5R)-3-(2-bromoacetyl)-5-methoxycarbonyl-4-phenyl-2-thiazolidinecarboxylate (eluted first), in the form of a yellow oil which is used without further purification in the subsequent syntheses, and 0.23 g of tert-butyl (2S,4S,5S)-3-(2-bromoacetyl)-5-methoxycarbonyl-4-phenyl-2-thiazolidinecarboxylate which, after beating in diisopropyl ether, is in the form of a cream-coloured solid melting at 137° C., are thus obtained.

D. tert-Butyl (4S)-5-methoxycarbonyl-4-phenyl-2-thiazolidinecarboxylate, as a mixture of the isomers at positions 2 and 5, may be prepared in the following way: to a solution of 18 g of methyl (2RS,3S)-3-amino-2-mercapto-3-phenylpropionate hydrochloride in 400 ml of methanol are added, under an argon atmosphere, 15.3 ml of triethylamine and 34.4 g of tert-butyl 2,2-dimorpholinoacetate. The reaction medium is heated at reflux for 2.5 hours then, after cooling to a temperature in the region of 20° C., evaporated to dryness under reduced pressure. The oily residue obtained is diluted with 50 ml of ethyl acetate, washed successively with twice 50 ml of water and 50 ml of saturated sodium chloride solution, dried over magnesium sulphate and concentrated to dryness under reduced pressure at a temperature in the region of 40° C. The crude product is purified by chromatography on silica [eluent: petroleum ether/diisopropyl ether (80/20 by volume)]. 8 g of tert-butyl (4S)-5-methoxycarbonyl-4-phenyl-2-thiazolidinecarboxylate, as a mixture of the isomers at positions 2 and 5, are thus obtained in the form of a yellow oil which is used without further purification in the subsequent syntheses.

E. Methyl (2RS,3S)-3-amino-2-mercapto-3-phenylpropionate hydrochloride may be prepared in the following way: a solution of 13.5 g of methyl (2RS,3S)-3-tert-butoxycarbonylamino-2-mercapto-3-phenylpropionate in 150 ml of methanol is introduced into a round-bottomed flask purged with argon and protected from the light. 45 ml of an 8N methanolic solution of hydrochloric acid are added slowly to this mixture, cooled to a temperature in the region of 5° C. The stirring is continued for 3 hours at a temperature in the region of 20° C., then the reaction medium is concentrated to dryness under reduced pressure at 30° C. After beating in 40 ml of ethyl acetate, 9 g of methyl (2RS,3S)-3-amino-2-mercapto-3-phenylpropionate hydrochloride are thus obtained in the form of an ochre solid which is used without further purification in the subsequent syntheses.

F. Methyl (2RS,3S)-3-tert-butoxycarbonylamino-2-mercapto-3-phenylpropionate may be prepared in the following way: to a solution of 39 g of methyl (2RS,3S)-3-tert-butoxycarbonylamino-2-acetylthio-3-phenylpropionate in 400 ml of methanol are added 8.2 g of sodium methoxide. The reaction mixture is stirred for 3 hours at a temperature in the region of 25° C. and then concentrated to dryness under reduced pressure at 30° C. The residue obtained is diluted with 200 ml of ethyl acetate and 200 ml of aqueous 1N hydrochloric acid solution. The organic phase is separated out after settling of the phases has taken place and the aqueous phase is extracted with twice 50 ml of ethyl acetate. The combined organic phases are washed with 50 ml of saturated aqueous sodium chloride solution, dried over magnesium sulphate and concentrated to dryness under reduced pressure at 40° C. 38.0 g of methyl (2RS,3S)-3-tert-butoxycarbonylamino-2-mercapto-3-phenylpropionate are thus obtained in the form of a yellow oil which is used without further purification in the subsequent syntheses.

G. Methyl (2RS,3S)-3-tert-butoxycarbonylamino-2-acetylthio-3-phenylpropionate may be prepared in the following way: to a solution of 50 g of methyl (2R,3S)-3-tert-butoxycarbonylamino-2-tosyloxy-3-phenylpropionate in 400 ml of acetone are added 28.2 g of potassium thioacetate. The reaction medium is heated at reflux for 4 hours and then evaporated to dryness under reduced pressure at 30° C. The residue obtained is diluted with 200 ml of ethyl acetate and 200 ml of water. The organic phase is separated out after settling of the phases has taken place, washed with twice 100 ml of water and with 100 ml of saturated aqueous sodium chloride solution, dried over magnesium sulphate and concentrated to dryness under reduced pressure at 40° C. 41.0 g of methyl (2RS,3S)-3-tert-butoxycarbonylamino-2-acetylthio-3-phenylpropionate are thus obtained in the form of a brown oil which is used without further purification in the subsequent syntheses.

H. Methyl (2R,3S)-3-tert-butoxycarbonylamino-2-tosyloxy-3-phenylpropionate may be prepared in the following way: to a mixture of 100 g of methyl (2R,3S)-3-tert-butoxycarbonylamino-2-hydroxy-3-phenylpropionate and 72 ml of triethylamine in 500 ml of dichloromethane is added, at a temperature in the region of 5° C., a solution of 71 g of tosyl chloride in 500 ml of dichloromethane. After warming to a temperature in the region of 20° C., the reaction medium is stirred for 12 hours and then concentrated to dryness under reduced pressure at 30° C. The residue obtained is diluted with 500 ml of ethyl acetate and 500 ml of water. The organic phase is separated out after settling of the phases has taken place, washed with twice 200 ml of water and with 200 ml of saturated aqueous sodium chloride solution, dried over magnesium sulphate and concentrated to dryness under reduced pressure at 40° C. 148.0 g of methyl (2R,3S)-3-tert-butoxycarbonylamino-2-tosyloxy-3-phenylpropionate are thus obtained in the form of a white solid melting at 120° C.

Methyl (2R,3S)-3-tert-butoxycarbonylamino-2-hydroxy-3-phenylpropionate may be prepared according to the process described in Patent WO 93/17997.

tert-Butyl 2,2-dimorpholinoacetate may be prepared according to the procedure described by R. Heymes et al., Bull. Soc. Chim. Fr., 2343-9 (1973).

EXAMPLE 2

The process is performed in a similar manner to that described in Example 1, but starting with a solution containing 0.7 g of tert-butyl (2S,4S,5S)-3-(2-aminoacetyl)-5-methoxycarbonyl-4-phenyl-2-thiazolidinecarboxylate in 20 ml of tetrahydrofuran and 250 µl of 3-methylphenyl isocyanate. The crude product is purified by chromatography on silica [eluent: ethyl acetate/cyclohexane (20/80 by volume)]. The fractions containing the expected product are combined and concentrated to dryness under reduced pressure at 40° C.

0.28 g of tert-butyl (2S,4S,5S)-5-methoxycarbonyl-3-{2-[3-(3-methylphenyl)ureido]acetyl}-4-phenyl-2-thiazolidinecarboxylate is thus obtained in the form of a white foam, Rf=0.39 [ethyl acetate/cyclohexane (50/50 in volume)]; $^1$H NMR (200 MHz, (CD$_3$)$_2$SO with addition of a few drops of CD$_3$COOD, at a temperature of 297 K, δ in ppm): 1.48 (s, 9H: CH$_3$ of the tert-butyl); 2.21 (s, 3H: ArCH$_3$); 3.28 and 4.15 (broad d and d respectively, J=17.5 Hz, 1H each: COCH$_2$N); 3.37 (s, 3H: COOCH$_3$); 5.10 (d, J=7 Hz, 1H: H at C5 of the ring); 5.43 (s, 1H: H at C2 of the ring); 5.68 (d, J=7 Hz, 1H: H at C4 of the ring); 6.70 (broad d, J=7.5 Hz, 1H: aromatic H (H ortho to the CH$_3$)); 7.06 (t, J=7.5 Hz, 1H: aromatic H (H meta to the CH$_3$)); from 7.00 to 7.50 (mt, 5H: aromatic H); 7.72 (mt, 2H: H ortho to the phenyl).

A. tert-Butyl (2S,4S,5S)-3-(2-aminoacetyl)-5-methoxycarbonyl-4-phenyl-2-thiazolidinecarboxylate may be prepared in a similar manner to that described in Example 1A, but starting with 0.77 g of tert-butyl (2S,4S,5S-3-(2-azidoacetyl)-5-methoxycarbonyl-4-phenyl 2-thiazolidinecarboxylate, 0.50 g of triphenylphosphine and 34 μl of water. After stirring for 2 hours at a temperature in the region of 25° C., the crude solution obtained containing about 0.7 g of tert-butyl (2S,4S,5S)-3-(2-aminoacetyl)-5-methoxycarbonyl-4-phenyl-2-thiazolidinecarboxylate is used without further purification in the subsequent syntheses.

B. tert-Butyl (2S,4S,5S)-3-(2-azidoacetyl)-5-methoxycarbonyl-4-phenyl-2-thiazolidinecarboxylate may be prepared in a similar manner to that described in Example 1B, but starting with 0.58 g of tert-butyl (2S,4S,5S)-3-(2-bromoacetyl)-5-methoxycarbonyl-4-phenyl-2-thiazolidinecarboxylate and 0.09 g of sodium azide. 0.5 g of tert-butyl (2S,4S,5S)-3-(2-azidoacetyl)-5-methoxycarbonyl-4-phenyl-2-thiazolidinecarboxylate is thus obtained in the form of a yellow oil which is used without further purification in the subsequent syntheses.

EXAMPLE 3

To a solution of 0.13 g of tert-butyl (2S,4S,5S)-5-methoxycarbonyl-3-{2-[3-(3-methylphenyl)ureido]acetyl}-4-phenyl-2-thiazolidinecarboxylate in 10 ml of tetrahydrofuran are added, at a temperature in the region of 20° C., 2.5 ml of aqueous 0.1N sodium hydroxide solution. The reaction medium is stirred for 12 hours at this temperature and is then diluted with 20 ml of water and washed with twice 20 ml of diethyl ether. The aqueous phase, separated out after settling of the phases has taken place, is brought to pH 2 by addition of aqueous 1N sulphuric acid solution and extracted with 3 times 20 ml of diethyl ether. The combined organic phases are dried over magnesium sulphate and concentrated to dryness under reduced pressure at 30° C. 0.1 g of foam is obtained, which is dissolved in 2.0 ml of aqueous 0.1N sodium hydroxide solution. The insoluble material is separated out by filtration and the aqueous phase is brought to pH 2 by addition of aqueous 1N sulphuric acid solution. The precipitated product is isolated by filtration, washed with twice 2 ml of water and air-dried. 0.07 g of (2S,4S,5R)-2-tert-butoxycarbonyl-3-{2-[3-(3-methylphenyl)ureido]-acetyl}-4-phenyl-5-thiazolidinecarboxylic acid is thus obtained in the form of a white solid melting at 130° C., $[α]_D^{25}$=−5.1°±1.0° (c=0.49; methanol); $^1$H NMR (200 MHz, (CD$_3$)$_2$SO with addition of a few drops of CD$_3$COOD, at a temperature of 393 K, δ in ppm): 1.51 (s, 9H: CH$_3$ of the tert-butyl); 2.26 (s, 3H: ArCH$_3$); 3.70 and 4.05 (broad d and d respectively, J=17 Hz, 1H each: COCH$_2$N); 4.21 (d, J=4 Hz, 1H: H at C5 of the ring); 5.73 (s, 1H: H at C2 of the ring); 5.79 (d, J=4 Hz, 1H: H at C4 of the ring); 6.76 (broad d, J=7.5 Hz, 1H: aromatic H (H ortho to the CH$_3$)); 7.10 (t, J=7.5 Hz, 1H: aromatic H (H meta to the CH$_3$)); from 7.10 to 7.50 (mt, 5H: aromatic H); 7.72 (dd, J=7.5 and 2 Hz, 2H: H ortho to the phenyl).

EXAMPLE 4

10 ml of methanol are added slowly, under an inert atmosphere, to a round-bottomed flask containing 0.3 g of (2S,4S,5R)-2-tert-butoxycarbonyl-3-{2-[3-(3-benzyloxycarbonylmethylphenyl)ureido]-acetyl}-4-phenyl-5-thiazolidinecarboxylic acid, 0.18 g of ammonium formate and 0.3 g of 10% palladium-on-charcoal. The reaction medium is heated at reflux for 1 hour and then cooled to a temperature in the region of 25° C. The catalyst is separated out by filtration and the filtrate is concentrated to dryness under reduced pressure at 40° C. The residue obtained is dissolved in 9.4 ml of aqueous 0.1N sodium hydroxide solution. The aqueous solution obtained is filtered and brought to pH 2 by addition of aqueous 0.1N hydrochloric acid solution. The precipitated product is isolated by filtration, washed with twice 5 ml of water and air-dried. 0.19 g of 3-{3-[2-((2S,4S,5R)-2-tert-butoxycarbonyl-5-carboxy-4-phenyl-3-thiazolidinyl)-2-oxoethyl]ureido}phenylacetic acid is thus obtained in the form of a white solid melting at 130° C., $[α]_D^{25}$=−3.9°±1.0 (c=0.407; MeOH); $^1$H NMR (200 MHz, (CD$_3$)$_2$SO with addition of a few drops of CD$_3$COOD, at a temperature of 373 K, δ in ppm): 1.49 (s, 9H: CH$_3$ of the tert-butyl); 3.49 (s, 2H: ArCH$_2$COO); 3.65 and 4.03 (broad d and d respectively, J=17 Hz, 1H each: COCH$_2$N); 4.19 (d, J=3.5 Hz, 1H: H at C5 of the ring); 5.70 (s, 1H: H at C2 of the ring); 5.76 (d, J=3.5 Hz, 1H: H at C4 of the ring); 6.83 (broad d, J=7.5 Hz, 1H: aromatic H (H ortho to the CH$_2$)); 7.14 (t, J=7.5 Hz, 1H: aromatic H (H meta to the CH$_2$)); from 7.20 to 7.50 (mt, 5H: aromatic H); 7.72 (broad d, J=7.5 Hz, 2H: H ortho to the phenyl).

A. (2S,4S,5R)-2-tert-Butoxycarbonyl-3-{2-[3-(3-benzyloxycarbonylmethylphenyl)ureido]acetyl}-4-phenyl-5-thiazolidinecarboxylic acid may be prepared in a similar manner to that described in Example 3, but starting with 0.65 g of methyl (2S,4S,5R)-2-tert-butoxycarbonyl-3-{2-[3-(3-benzyloxycarbonylmethylphenyl)ureido]acetyl}-4-phenyl-5-thiazolidinecarboxylate and 7 ml of aqueous 0.1N sodium hydroxide solution in 10 ml of tetrahydrofuran. 0.37 g of (2S,4S,5R)-2-tert-butoxycarbonyl-3-{2-[3-(3-benzyloxycarbonylmethylphenyl)ureido]acetyl}-4-phenyl-5-thiazolidinecarboxylic acid is thus obtained in the form of a white solid melting at 114° C.

B. Methyl (2S,4S,5R)-2-tert-butoxycarbonyl-3-{2-[3-(3-benzyloxycarbonylmethylphenyl)ureido]acetyl}-4-phenyl-5-thiazolidinecarboxylate may be prepared in a similar manner to that described in Example 1, but starting with 0.57 g of tert-butyl (2S,4S,5R)- 3-(2-aminoacetyl)-5-methoxycarbonyl-4-phenyl-2-thiazolidinecarboxylate and 0.5 g of benzyl 3-isocyanatophenylacetate. The crude product is purified by chromatography on silica [eluent: ethyl acetate/cyclohexane (40/60 by volume)]. The fractions containing the expected product are combined and concentrated to dryness under reduced pressure at 30° C. 0.3 g of methyl (2S,4S,5R)-2-tert-butoxycarbonyl-3-{2-[3-(3-benzyloxycarbonylmethylphenyl)ureido]acetyl}-4-phenyl-5-thiazolidinecarboxylate is thus obtained in the form of an amorphous product which is used without further purification in the subsequent syntheses.

C. Benzyl 3-isocyanatophenylacetate may be prepared in the following way: to a suspension of 0.5 g of charcoal in a mixture of 2.6 ml of trichloromethyl chloroformate and 75 ml of toluene is added over 15 minutes, at a temperature in the region of −30° C., a solution of 5.0 g of benzyl 3-aminophenylacetate in 40 ml of toluene. The reaction mixture is stirred for 2 hours and then heated at reflux for 3 hours. After cooling to a temperature in the region of 25° C., the reaction medium is degassed by sparging with nitrogen; the catalyst is separated out by filtration and the filtrate is concentrated to dryness under reduced pressure at 40° C. 6.4 g of benzyl 3-isocyanatophenylacetate are thus obtained in the form of a yellow oil which is used without further purification in the subsequent syntheses.

D. Benzyl 3-aminophenylacetate may be prepared in the following way: to a mixture of 28 g of benzyl 3-nitrophenylacetate in 125 ml of methanol and 1300 ml of water are added 265 g of ammonium chloride and 130 g of zinc powder. The reaction medium is heated at reflux for 1 hour and then cooled to a temperature in the region of 0° C. The insoluble salts are separated out by filtration and the filtrate is extracted with 3 times 500 ml of diethyl ether. The organic phases collected are washed successively with 100 ml of water and with 200 ml of saturated aqueous sodium chloride solution. After drying over magnesium sulphate and concentration to dryness under reduced pressure, 20.5 g of benzyl 3-aminophenylacetate are thus obtained in the form of a yellow oil which is used without further purification in the subsequent syntheses.

E. Benzyl 3-nitrophenylacetate may be prepared in the following way: to a mixture containing 21.0 g of 3-nitrophenylacetic acid and 0.5 ml of dimethylformamide in 200 ml of 1,2-dichloroethane are added slowly 10.3 ml of oxalyl chloride. The reaction medium is stirred for 3 hours at a temperature in the region of 25° C., followed by addition of 12.5 g of benzyl alcohol. The stirring is continued for 12 hours at this same temperature, and the reaction medium is then washed with twice 100 ml of saturated aqueous sodium hydrogen carbonate solution, with 100 ml of water and with 100 ml of saturated aqueous sodium chloride solution. The organic phase collected is dried over magnesium sulphate and concentrated to dryness under reduced pressure at 40° C. The residue obtained is purified by chromatography on silica [eluent: ethyl acetate/cyclohexane (30/70 by volume)]. The fractions containing the expected product are combined and concentrated to dryness under reduced pressure at 40° C. 28.0 g of benzyl 3-nitrophenylacetate are thus obtained in the form of a yellow oil which is used without further purification in the subsequent syntheses.

EXAMPLE 5

The process is performed as in Example 3, but starting with 0.3 g of methyl (2S,4S,5S)-3-{2-{3-[(S)-3-(1-benzyloxycarbonylethyl)phenyl]ureido}acetyl}-2-tert-butoxycarbonyl-4-phenyl-5-thiazolidinecarboxylate and 4.5 ml of aqueous 0.1N sodium hydroxide solution. 0.15 g of (2S,4S,5R)-3-{2-{3-[(S)-3-(1-benzyloxycarbonylethyl)phenyl]ureido}acetyl}-2-tert-butoxycarbonyl-4-phenyl-5-thiazolidinecarboxylic acid is thus obtained in the form of a white solid melting at 96° C., $[\alpha]_D^{25}=+6°\pm1°$ (c=0.46; MeOH); $^1$H NMR (250 MHz, (CD$_3$)$_2$SO with addition of a few drops of CD$_3$COOD, at a temperature of 393 K, δ in ppm): 1.45 (d, J=7.5 Hz, 3H: CH$_3$); 1.51 (s, 9H: CH$_3$ of the tert-butyl); 3.66 and 4.05 (broad d and d respectively, J=17.5 Hz, 1H each: COCH$_2$N); 3.77 (q, J=7.5 Hz, 1H: CHCOO); 4.19 (d, J=4 Hz, 1H: H at C5 of the ring); 5.12 (s, 2H: OCH$_2$); 5.71 (s, 1H: H at C2 of the ring); 5.77 (d, J=4 Hz, 1H: H at C4 of the ring); 6.85 (broad d, J=7.5 Hz, 1H: aromatic H (H ortho to the CH)); 7.15 (t, J=7.5 Hz, 1H: aromatic H (meta to the CH); from 7.20 to 7.50 (mt, 10H: aromatic H); 7.72 (broad d, J=7.5 Hz, 2H: H ortho to the phenyl at position 4).

A. Methyl (2S,4S,5S)-3-{2-{3-[(S)-3-(1-benzyloxycarbonylethyl)phenyl]ureido}acetyl}-2-tert-butoxycarbonyl-4-phenyl-5-thiazolidinecarboxylate may be prepared in a similar manner to that described in Example 1, but starting with 0.50 g of tert-butyl (2S,4S,5S)-3-(2-aminoacetyl)-5-methoxycarbonyl-4-phenyl-2-thiazolidinecarboxylate and 0.5 g of benzyl (S)-2-(3-isocyanatophenyl)propionate. The crude product is purified by chromatography on silica [eluent: ethyl acetate/cyclohexane (40/60 by volume)]. The fractions containing the expected product are combined and concentrated to dryness under reduced pressure at 30° C. 0.31 g of methyl (2S,4S,5S)-3-{2-{3-[(S)-3-(1-benzyloxycarbonylethyl)phenyl]ureido}acetyl}-2-tert-butoxycarbonyl-4-phenyl-5-thiazolidinecarboxylate is thus obtained in the form of an amorphous product which is used without further purification in the subsequent syntheses.

B. Benzyl (S)-2-(3-isocyanatophenyl)propionate may be prepared in a similar manner to that described in Example 4C, but starting with 2.85 g of benzyl (S)-2-(3-aminophenyl)propionate, 0.24 g of charcoal and 1.5 ml of trichloromethyl chloroformate. 3.1 g of benzyl (S)-2-(3-isocyanatophenyl)propionate are thus obtained in the form of a yellow oil which is used without further purification in the subsequent syntheses.

C. Benzyl (S)-2-(3-aminophenyl)propionate may be prepared in a similar manner to that described in Example 4D, but starting with 8 g of benzyl (S)-2-(3-nitrophenyl)propionate, 75 g of ammonium chloride and 37 g of zinc powder. 6.7 g of benzyl (S)-2-(3-aminophenyl)propionate are thus obtained in the form of a yellow oil which is used without further purification in the subsequent syntheses.

D. Benzyl (S)-2-(3-nitrophenyl)propionate may be prepared in a similar manner to that described in Example 4E, but starting with 9.75 g of (S)-2-(3-nitrophenyl)propionic acid, 4.7 ml of oxalyl chloride, 0.5 ml of dimethylformamide and 5.4 g of benzyl alcohol. The crude product is purified by chromatography on silica [eluent: ethyl acetate/cyclohexane (30/70 by volume)]. The fractions containing the expected product are combined and concentrated to dryness under reduced pressure at 40° C. 11.5 g of benzyl (S)-2-(3-nitrophenyl)propionate are thus obtained in the form of a yellow oil which is used without further purification in the subsequent syntheses.

(S)-2-(3-Nitrophenyl)propionic acid may be prepared according to the procedure described by F. Nerdel and H. H ärter, Liebigs Ann. Chem., 621, 22–33 (1959).

EXAMPLE 6

The process is performed as in Example 4, but starting with 0.58 g of (2S,4S,5R)-3-{2-{3-[(S)-3-(1-benzyloxycarbonylethyl)phenyl]ureido}acetyl}-2-tert-butoxycarbonyl-4-phenyl-5-thiazolidinecarboxylic acid, 0.34 g of ammonium formate and 0.6 g of 10% palladium-on-charcoal. 0.21 g of 2-{3-{3-[2-((2S,4S,5R)-2-tert-butoxycarbonyl-5-carboxy-4-phenyl-3-thiazolidinyl)-2-oxoethyl]ureido}phenyl}propionic acid is thus obtained in the form of a white solid melting at 142° C., $[\alpha]_D^{25}=+24.5°\pm0.6°$ (c=1.01; MeOH); $^1$H NMR (200 MHz, (CD$_3$)$_2$SO with addition of a few drops of CD$_3$COOD, at a temperature of 373 K, δ in ppm): 1.41 (d, J=7 Hz, 3H: CH$_3$); 1.51 (s, 9H: CH$_3$ of the tert-butyl); 3.62 (q, J=7 Hz, 1H: CHCOO); 3.66 and 4.05 (broad d and d respectively, J=17.5

Hz, 1H each: COCH$_2$N); 4.18 (d, J=4 Hz, 1H: H at C5 of the ring); 5.72 (s, 1H: H at C2 of the ring); 5.77 (d, J=4 Hz, 1H: H at C4 of the ring); 6.86 (broad d, J=7.5 Hz, 1H: aromatic H (H ortho to the CH)); 7.17 (t, J=7.5 Hz, 1H: aromatic H (H meta to the CH); from 7.20 to 7.50 (mt, 5H: aromatic H); 7.73 (dd, J=7.5 and 1.5 Hz, 2H: H ortho to the phenyl).

EXAMPLE 7

The process is performed in a similar manner to that described in Example 1, but starting with 0.30 g of tert-butyl (2S,4S,5S)-3-(2-aminoacetyl)-5-methoxycarbonyl-4-(2-fluorophenyl)-2-thiazolidinecarboxylate dissolved in 10 ml of tetrahydrofuran and 100 μl of 3-methylphenyl isocyanate. The crude product is purified by chromatography on silica [eluent: ethyl acetate/cyclohexane (30/70 by volume)]. The fractions containing the expected product are combined and concentrated to dryness under reduced pressure at 40° C. 0.08 g of tert-butyl (2S,4S,5S)-5-methoxycarbonyl-3-{2-[3-(3-methylphenyl)ureido]acetyl}-4-(2-fluorophenyl)-2-thiazolidinecarboxylate is thus obtained in the form of a yellow foam, Rf=0.43 [ethyl acetate/cyclohexane (40/60 by volume); $^1$H NMR (200 MHz, (CD$_3$)$_2$SO with addition of a few drops of CD$_3$COOD, at a temperature of 393 K, δ in ppm): 1.52 (s, 9H: CH$_3$ of the tert-butyl); 2.25 (s, 3H: ArCH$_3$); 3.34 (s, 3H: COOCH$_3$); 3.70 and 4.05 (broad d and d respectively, J=17 Hz, 1H each: COCH$_2$N); 4.95 (d, J=7.5 Hz, 1H: H at C5 of the ring); 5.75 (s, 1H: H at C2 of the ring); 6.05 (d, J=7.5 Hz: 1H: H at C4 of the ring); 6.76 (broad d, J=7.5 Hz, 1H: aromatic H (H ortho to the CH$_3$)); 7.09 (t, J=7.5 Hz, 1H: aromatic H (H meta to the CH$_3$)); from 7.10 to 7.50 (mt, 5H: aromatic H); 8.00 (mt, 1H: aromatic H (H meta to the F)).

A. tert-Butyl (2S,4S,5S)-3-(2-aminoacetyl)-5-methoxycarbonyl-4-(2-fluorophenyl)-2-thiazolidinecarboxylate may be prepared in a similar manner to that described in Example 1A, but starting with 0.5 g of tert-butyl (2S,4S,5S)-3-(2-azidoacetyl)-5-methoxycarbonyl-4-(2-fluorophenyl)-2-thiazolidinecarboxylate, 0.20 g of triphenylphosphine and 14 μl of water. The crude solution obtained containing about 0.30 g of tert-butyl (2S,4S,5S)-3-(2-aminoacetyl)-5-methoxycarbonyl-4-(2-fluorophenyl)-2-thiazolidinecarboxylate is used without further purification in the subsequent syntheses.

B. tert-Butyl (2S,4S,5S)-3-(2-azidoacetyl)-5-methoxycarbonyl-4-(2-fluorophenyl)-2-thiazolidinecarboxylate may be prepared in a similar manner to that described in Example 1B, but starting with 0.35 g of tert-butyl (2S,4S,5S)-3-(2-bromoacetyl)-5methoxycarbonyl-4-(2-fluorophenyl)-2-thiazolidinecarboxylate and 0.05 g of sodium azide. 0.5 g of tert-butyl (2S,4S,5S)-3-(2-azidoacetyl)-5-methoxycarbonyl-4-(2-fluorophenyl)-2-thiazolidinecarboxylate is thus obtained in the form of a yellow oil which is used without further purification in the subsequent syntheses.

C. tert-Butyl (2S,4S,5S)-3-(2-bromoacetyl)-5-methoxycarbonyl-4-(2-fluorophenyl)-2-thiazolidinecarboxylate may be prepared in a similar manner to that described in Example 1C, but starting with 0.8 g of tert-butyl (2RS,4S,5S)-5-methoxycarbonyl-4-(2-fluorophenyl)-2-thiazolidinecarboxylate, 0.3 ml of triethylamine and 0.47 g of bromoacetyl bromide. The crude product obtained is purified by chromatography on silica [eluent: ethyl acetate/cyclohexane (30/70 by volume)]. The fractions containing the product are combined and concentrated to dryness under reduced pressure at 30° C. 0.35 g of tert-butyl (2S,4S,5S)-3-(2-bromoacetyl)-5-methoxycarbonyl-4-(2-fluorophenyl)-2-thiazolidinecarboxylate is thus obtained in the form of a yellow oil which is used without further purification in the subsequent syntheses.

D. tert-Butyl (2RS,4S,5S)-5-methoxycarbonyl-4-(2-fluorophenyl)-2-thiazolidinecarboxylate may be prepared in a similar manner to that described in Example 1D, but starting with 1.0 g of methyl (2S,3S)-3-amino-2-mercapto-3-(2-fluorophenyl)propionate hydrochloride, 1.0 ml of triethylamine and 2.1 g of tert-butyl 2,2-dimorpholinoacetate. The crude product obtained is purified by chromatography on silica [eluent: ethyl acetate/cyclohexane (20/80 by volume)]. 0.8 g of tert-butyl (2RS,4S,5S)-5-methoxycarbonyl-4-(2-fluorophenyl)-2-thiazolidinecarboxylate is thus obtained in the form of a yellow oil which is used without further purification in the subsequent syntheses.

E. Methyl (2S,3S) 3-amino-2-mercapto-3-(2-fluorophenyl)propionate hydrochloride may be prepared in a similar manner to that described in Example 1E, but starting with 8.2 g of methyl (2RS,3S)-3-tert-butoxycarbonylamino-2-mercapto-3-(2-fluorophenyl)propionate and 20 ml of a methanolic 5N solution of hydrochloric acid. Stirring is continued for 3 h at a temperature in the region of 20° C. and the reaction medium is then concentrated to dryness under reduced pressure at 30° C. The residue obtained is beaten in 20 ml of ethyl acetate. The solid obtained is separated out by filtration and air-dried. 2.3 g of methyl (2S,3S) 3-amino-2-mercapto-3-phenylpropionate hydrochloride are thus obtained in the form of a white solid melting at 172° C. After evaporation of the filtrate, 1.8 g of methyl (2RS,3S)-3-amino-2-mercapto-3-phenylpropionate hydrochloride are also isolated, in the form of a white solid which is used without further purification in the subsequent syntheses.

F. Methyl (2RS,3S)-3-tert-butoxycarbonylamino-2-mercapto-3-(2-fluorophenyl)propionate may be prepared in a similar manner to that described in Example 1F, but starting with 9.8 g of methyl (2RS,3S)-3-tert-butoxycarbonylamino-2-acetylthio-3-phenylpropionate and 1.35 g of sodium methoxide. 8.2 g of methyl (2RS,3S)-3-tert-butoxycarbonylamino-2-mercapto-3-(2-fluorophenyl) propionate are thus obtained in the form of a red oil which is used without further purification in the subsequent syntheses.

G. Methyl (2RS,3S)-3-tert-butoxycarbonylamino-2-acetylthio-3-(2-fluorophenyl) propionate may be prepared in a similar manner to that described in Example 1G, but starting with 30 g of methyl (2R,3S)-3-tert-butoxycarbonylamino-2-tosyloxy-3-(2-fluorophenyl) propionate and 17.2 g of potassium thioacetate. 9.8 g of methyl (2RS,3S)-3-tert-butoxycarbonylamino-2-acetylthio-3-phenylpropionate are thus obtained in the form of a red oil which is used without further purification in the subsequent syntheses.

H. Methyl (2R,3S)-3-tert-butoxycarbonylamino-2-tosyloxy-3-(2-fluorophenyl)propionate may be prepared in a similar manner to that described in Example 1H, but starting with 20 g of methyl (2R,3S)-3-tert-butoxycarbonylamino-2-hydroxy-3-(2-fluorophenyl)propionate, 13.4 ml of triethylamine and 13.3 g of tosyl chloride. 30.8 g of methyl (2R,3S)-3-tert-butoxycarbonylamino-2-tosyloxy-3-(2-fluorophenyl)propionate are thus obtained in the form of a white solid melting at 110° C., which product is used without further purification in the subsequent syntheses.

I. Methyl (2R,3S)-3-tert-butoxycarbonylamino-2-hydroxy-3-(2-fluorophenyl)propionate may be prepared in the following way: to 2 g of a suspension of 5% palladium on activated charcoal powder in 10 ml of ethanol is added a solution of 50 g of methyl (2R,3S)-2-hydroxy-3-((S)-1-phenylethylamino)-3-(2-fluorophenyl)propionate in a mixture of 200 ml of methanol and 20 ml of acetic acid. The reaction mixture is stirred for 8 hours under a hydrogen atmosphere (150 kPa) at a temperature in the region of 25° C. The catalyst is separated out by filtration and washed with twice 50 ml of methanol. 27 ml of aqueous 30% sodium hydroxide solution are added, at a temperature in the region of 5° C., to the methanolic solution of methyl (2R,3S)-3-amino-2-hydroxy-3-(2-fluorophenyl)propionate thus obtained, followed, after warming to a temperature in the region of 25° C., by a solution of 34.2 g of di-tert-butyl dicarbonate in 70 ml of methanol and 100 ml of water. The reaction medium is stirred for 12 hours and then cooled to a temperature in the region of 5° C. and diluted with 200 ml of water. The heterogeneous medium obtained is beaten for 1 hour at this temperature and the solid is isolated by filtration. After drying, 39.6 g of methyl (2R,3S)-3-tert-butoxycarbonylamino-2-hydroxy-3-(2-fluorophenyl) propionate are thus obtained in the form of a white solid melting at 95° C., $[\alpha]_D^{25}=-6.3°\pm0.9°$ (C=0.627, MeOH).

J. Methyl (2R,3S)-2-hydroxy-3-((S)-1-phenylethylamino)-3-(2-fluorophenyl)propionate may be prepared in the following way: to a suspension of 50 g of (3R,4S)-3-hydroxy-4-(2-fluorophenyl)-1-((S)-1-phenylethyl)-2-azetidinone in 120 ml of methanol, cooled to a temperature in the region of 5° C., are added slowly 47.5 ml of an 8N methanolic solution of hydrochloric acid, while maintaining the temperature below 20° C. The reaction mixture is stirred for 12 hours at this temperature, cooled to a temperature in the region of 5° C. and basified to pH 7 by slow addition of 35 ml of aqueous 30% sodium hydroxide solution. 700 ml of water are added at a temperature in the region of 0° C. Stirring is continued for 1 hour and the solid obtained is then isolated by filtration, washed with twice 100 ml of water cooled to a temperature in the region of 5° C. and air-dried. 53.6 g of methyl (2R,3S)-2-hydroxy-3-((S)-1-phenylethylamino)-3-(2-fluorophenyl)propionate are thus obtained in the form of a white solid melting at a temperature below 50° C., which product is used without further purification in the subsequent syntheses.

K. (3R,4S)-3-Hydroxy-4-(2-fluorophenyl)-1-((S)-1-phenylethyl)-2-azetidinone may be prepared in the following way: to a solution, cooled to a temperature in the region of 0° C., of 110 g of a mixture in a 65/35 molar proportion of the two diastereoisomers of 3-acetoxy-4-(2-fluorophenyl)-1-((S)-1-phenylethyl)-2-azetidinone, A and B forms, in 600 ml of methanol are added 11 ml of aqueous 30% sodium hydroxide solution. The reaction medium is stirred for 1 hour at a temperature in the region of 0° C., and diluted by addition of 250 ml of water and 60 ml of methanol. Stirring is continued for 2 hours at this temperature and the solid is then isolated by filtration, washed with 50 ml of water cooled to a temperature in the region of 5° C. and air-dried. 50.5 g of (3R,4S)-3-hydroxy-4-(2-fluorophenyl)-1-((S)-1-phenylethyl)-2-azetidinone are thus obtained in the form of a white solid melting at 138° C.

L. The mixture of the A and B forms of the two diastereoisomers of 3-acetoxy-4-(2-fluorophenyl)-1-((S)-1-phenylethyl)-2-azetidinone may be prepared in the following way: to a mixture containing a solution of 190 g of (S)-1-phenyl-N-(2-fluorobenzylidene)ethylamine in 200 ml of toluene and 148 ml of N-ethylmorpholine are added dropwise, over 2 hours and at a temperature in the region of 20° C., 84 ml of 2-acetoxyacetyl chloride. The reaction mixture is stirred for 12 hours at this temperature, followed by addition of 500 ml of aqueous 2.5N hydrochloric acid solution. The organic phase is separated out after settling of the phases has taken place, washed with 100 ml of water and with twice 200 ml of saturated aqueous sodium hydrogen carbonate solution, dried over magnesium sulphate and concentrated to dryness under reduced pressure at 40° C. 220 g of a mixture in a 65/35 molar proportion of the A and B forms of the two diastereoisomers of 3-acetoxy-4-(2-fluorophenyl)-1-((S)-1-phenylethyl)-2-azetidinone are thus obtained in the form of a brown oil which is used without further purification in the subsequent syntheses.

M. (S)-1-Phenyl-N-(2-fluorobenzylidene) ethylamine may be prepared in the following way: to a solution of 100 g of 2-fluorobenzaldehyde in 500 ml of toluene are added 102 ml of (S)-1-phenylethylamine. The reaction medium is left for 12 hours at a temperature in the region of 20° C. The water formed is separated out after settling of the phases has taken place and the organic phase is dried by azeotropic distillation over 2 hours using a Dean-Stark apparatus. After evaporation of the solvents, 189 g of (S)-1-phenyl-N-(2-fluorobenzylidene) ethylamine are thus obtained in the form of a yellow oil which is used without further purification in the subsequent syntheses.

EXAMPLE 8

The process is performed in a similar manner to that described in Example 1, but starting with 0.34 g of tert-butyl (2S,4S,5R)-3-(2-aminoacetyl)-5-methoxycarbonyl-4-(2-fluorophenyl)-2-thiazolidinecarboxylate dissolved in 10 ml of tetrahydrofuran and 106 μl of 3-methylphenyl isocyanate. The crude product is purified by chromatography on silica [eluent: ethyl acetate/cyclohexane (20/80 by volume)]. The fractions containing the expected product are combined and concentrated to dryness under reduced pressure at 40° C. After beating in diisopropyl ether, 0.17 g of tert-butyl (2S,4S,5R)-5-methoxycarbonyl-3-{2-[3-(3-methylphenyl)ureido]acetyl}-4-(2-fluorophenyl)-2-thiazolidinecarboxylate is thus obtained in the form of a pale yellow foam, Rf=0.30, [ethyl/acetate cyclohexane (30/70 by volume); $^1$H NMR (250 MHz, $(CD_3)_2SO$, at a temperature of 363 K, δ in ppm): 1.53 (s, 9H: $CH_3$ of the tert-butyl); 2.27 (s, 3H: $ARCH_3$); 3.34 (s, 3H: $COOCH_3$); from 3.60 to 3.80 and 4.06 (mt and dd respectively (J=17 and 5 Hz), 1H each: $COCH_2N$); 4.33 (d, J=3 Hz, 1H: H at C5 of the ring); 5.74 (mt, 1H: H at C2 of the ring); 6.01 (d, J=3 Hz, 1H: H at C4 of the ring); 6.23 (t, J=5 Hz, 1H NHCO); 6.78 (broad d, J=7.5 Hz, 1H: aromatic H (H ortho to the $CH_3$)); 7.09 (t, J=7.5 Hz, 1H: aromatic H (H meta to the $CH_3$)); from 7.10 to 7.50 (mt, 5H: aromatic H); 8.03 (mt, 1H: aromatic H (H meta to the F)); 8.40 (s, 1H: ArNHCO).

A. tert-Butyl (2S,4S,5R)-3-(2-aminoacetyl)-5-methoxycarbonyl-4-(2-fluorophenyl)-2-thiazolidinecarboxylate may be prepared in a similar manner to that described in Example 1A, but starting with 0.56 g of tert-butyl (2S,4S,5R)-3-(2-azidoacetyl)-5-methoxycarbonyl-4-(2-fluorophenyl)-2-thiazolidinecarboxylate, 0.21 g of triphenylphosphine and 15 μl of water. The crude solution obtained containing about 0.34 g of tert-butyl (2S,4S,5R)-3-(2-aminoacetyl)-5-methoxycarbonyl-4-(2-fluorophenyl)-2-thiazolidinecarboxylate is used without further purification in the subsequent syntheses.

B. tert-Butyl (2S,4S,5R)-3-(2-azidoacetyl)-5-methoxycarbonyl-4-(2-fluorophenyl)-2-thiazolidinecarboxylate may be prepared in a similar manner to that described in Example 1B, but starting with 0.39 g of tert-butyl (2S,4S,5R)-3-(2-bromoacetyl)-5-methoxycarbonyl-4-(2-fluorophenyl)-2-thiazolidinecarboxylate and 0.055 g of sodium azide. 0.56 g of tert-butyl (2S,4S,5R)-3-(2-azidoacetyl)-5-methoxycarbonyl-4-(2-fluorophenyl)-2-thiazolidinecarboxylate is thus obtained in the form of a yellow oil which is used without further purification in the subsequent syntheses.

C. tert-Butyl (2S,4S,5R)-3-(2-bromoacetyl)-5-methoxycarbonyl-4-(2-fluorophenyl)-2-thiazolidinecarboxylate may be prepared in a similar manner to that described in Example 1C, but starting with 1.7 g of tert-butyl (2RS,4S,5RS)-5-methoxycarbonyl-4-(2-fluorophenyl)-2-thiazolidinecarboxylate, 0.7 ml of triethylamine and 1.0 g of bromoacetyl bromide. The crude 2 g mixture of the diastereoisomers obtained ((2S,4S,5R) and (2S,4S,5S)) is separated by high performance liquid chromatography using a preparative column of the 500-Prepak type (Waters) and an ethyl acetate/cyclohexane mixture (10/90 by volume) as mobile phase. 0.4 g of tert-butyl (2S,4S,5R)-3-(2-bromoacetyl)-5-methoxycarbonyl-4-(2-fluorophenyl)-2-thiazolidinecarboxylate (eluted first) and 0.61 g of tert-butyl (2S,4S,5S)-3-(2-bromoacetyl)-5-methoxycarbonyl-4-(2-fluorophenyl)-2-thiazolidinecarboxylate are thus obtained in the form of two yellow oils which are used without further purification in the subsequent syntheses.

D. tert-Butyl (2RS,4S,5RS)-5-methoxycarbonyl-4-(2-fluorophenyl)-2-thiazolidinecarboxylate may be prepared in a similar manner to that described in Example 1D, but starting with 1.8 g of methyl (2RS,3S)-3-amino-2-mercapto-3-(2-fluorophenyl)propionate hydrochloride, 1.9 ml of triethylamine and 3.9 g of tert-butyl 2,2-dimorpholinoacetate. The crude product obtained is purified by chromatography on silica [eluent: ethyl acetate/cyclohexane (20/80 by volume)]. 1.0 g of tert-butyl (2RS,4S,5RS)-5-methoxycarbonyl-4-(2-fluorophenyl)-2-thiazolidinecarboxylate is thus obtained in the form of a yellow oil which is used without further purification in the subsequent syntheses.

EXAMPLE 9

The process is performed in a similar manner to that described in Example 3, but starting with 0.35 g of tert-butyl (2S,4S,5S)-5-methoxycarbonyl-3-{2-[3-(3-methylphenyl)ureido]acetyl}-4-(2-fluorophenyl)-2-thiazolidinecarboxylate dissolved in 10 ml of tetrahydrofuran and 6.6 ml of aqueous 0.1N sodium hydroxide solution. 0.24 g of (2S,4S,5R)-2-tert-butoxycarbonyl-3-{2-[3-(3-methylphenyl)ureido]acetyl}-4-(2-fluorophenyl)-5-thiazolidinecarboxylic acid is thus obtained in the form of a white solid melting at 148° C., $[\alpha]_D^{25}=-17°\pm1°$ (c=0.504; MeOH); $^1$H NMR (200 MHz, (CD$_3$)$_2$SO with addition of a few drops of CD$_3$COOD, at a temperature of 373 K, 5 in ppm): 1.51 (s, 9H: CH$_3$ of the tert-butyl); 2.25 (s, 3H: ArCH$_3$); 3.76 and 4.04 (broad d and d respectively, J=18 Hz, 1H each: COCH$_2$N); 4.18 (d, J=3.5 Hz, 1H: H at C5 of the ring); 5.70 (s, 1H: H at C2 of the ring); 5.97 (d, J=3.5 Hz, 1H: H at C4 of the ring); 6.73 (broad d, J=7.5 Hz, 1H: aromatic H (H ortho to the CH$_3$)); 7.06 (t, J=7.5 Hz, 1H: aromatic H (H meta to the CH$_3$)); 7.10 to 7.50 (mt, 5H: aromatic H); 8.00 (mt, 1H: aromatic H at 6 (H meta to the F)).

The medicaments according to the invention consist of a compound of formula (I) in free form or in the form of a pharmaceutically acceptable salt, in pure form or in the form of a composition in which it is combined with any other pharmaceutically compatible product, which may be inert or physiologically active. The medicaments according to the invention may be used via the oral, parenteral, rectal or topical route.

As solid compositions for oral administration, tablets, pills, powders (gelatin capsules and cachets) or granules may be used. In these compositions, the active principle according to the invention is mixed with one or more inert diluents, such as starch, cellulose, sucrose, lactose or silica, under a stream of argon. These compositions may also comprise substances other than diluents, for example one or more lubricants such as magnesium stearate or talc, a dye, a coating (dragees) or a varnish.

As liquid compositions for oral administration, pharmaceutically acceptable solutions, suspensions, emulsions, syrups and elixirs, containing inert diluents such as water, ethanol, glycerol, vegetable oils or paraffin oil, may be used. These compositions may comprise substances other than diluents, for example wetting, sweetening, thickening, flavouring or stabilizing agents.

The sterile compositions for parenteral administration may preferably be emulsions, suspensions or aqueous or non-aqueous solutions. Water, propylene glycol, a polyethylene glycol, vegetable oils, in particular olive oil, injectable organic esters, for example ethyl oleate, or other suitable organic solvents may be used as solvent or vehicle. These compositions may also contain adjuvants, in particular wetting, tonicity, emulsifying, dispersing and stabilizing agents. The sterilization may be performed in several ways, for example by aseptic filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration may, for example, be creams, lotions, eye drops, mouth washes, nasal drops or aerosols.

In human therapy, the compounds according to the invention are particularly useful in the treatment and prevention of disorders linked to CCK and to gastrin in the nervous system and in the gastrointestinal system. These compounds may thus be used in the treatment and prevention of psychoses, anxiety disorders, depression, neurodegeneration, panic attacks, Parkinson's disease, tardive dyskinesia, irritable bowel syndrome, acute pancreatitis, ulcers, intestinal motility disorders, certain CCK-sensitive tumours and memory disorders, in the withdrawal from chronic treatments and alcohol or drug abuse, as constrictors of the pupil of the eye, as analgesics, as potentiators of the analgesic activity of narcotic and non-narcotic analgesic drugs and as appetite regulators.

The doses depend on the desired effect, the duration of the treatment and the route of administration used; they are generally between 0.05 g and 1 g per day via the oral route for an adult, with unit doses ranging from 10 mg to 500 mg of active substance.

In general, the doctor will determine the appropriate dosage depending on the age, the weight and all the other factors specific to the person to be treated.

The examples which follow illustrate compositions according to the invention:

EXAMPLE A

Gelatin capsules containing a 50 mg dose of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing a 50 mg dose of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) | 245 mg |
| qs 1 finished film-coated tablet weighing | |

EXAMPLE C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 cm³ |
| Sodium benzoate | 80 mg |
| 95% ethanol | 0.4 cm³ |
| Sodium hydroxide | 24 mg |
| Propylene glycol | 1.6 cm³ |
| Water qs | 4 cm³ |

We claim:
1. A compound of formula (I):

$$\begin{array}{c} R_1 \\ R_2 \end{array} \!\!\!\! \diagdown \!\!\!\! \begin{array}{c} S \\ \diagup \\ N \\ | \\ CO-CH-NH-CO-NH-R_6 \\ | \\ R_4 \end{array} \!\!\!\! R_3 \quad (I)$$

in which:

$R_1$ represents a $-(CH_2)_n-COOR_a$ or $-(CH_2)_n-CONR_bR_c$ radical;

$R_2$ represents a phenyl radical which may be substituted with one or more substituents selected from halogen atoms and alkyl, alkoxy, hydroxyl, nitro, amino, monoalkylamino, dialkylamino, alkoxycarbonyl, trifluoromethyl and trifluoromethoxy radicals;

$R_3$ represents a $-COORd$ or $-CONReRf$ radical;

$R_4$ represents a hydrogen atom or an alkyl radical;

$R_5$ represents a phenyl radical which may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, $-alk-O-CO-alk$, $-alk-COOX$, $-alk-O-alk$, $-alk'-COOX$, $-O-alk-COOX$, $-CH=CH-COOX$, $-CO-COOX$, $-alk-SO_3H$ in salt form, $-CH=CH-alk'$, $-C(=NOH)-COOX$, $-S-alk-COOX$, $-SO-alk-COOX$, $-SO_2-alk-COOX$, $-O-CH_2-alk'-COOX$, $-CX=N-O-alk-COOX$, $-alk-N(OH)-CO-alk$, $-alk-SO_2H$, $-SO_2-NH-CO-Rg$, $-SO_2-NH-SO_2-Rg$, $-CO-NH-CO-Rg$, $-CO-NH-SO_2-Rg$, $-B(OH)_2$, $-C(NH_2)=NOH$, $-SO_2-NH-Rh$, $-CO-NH-Rh$,

[chemical structures]

and 2,2-dimethyl-4,6-dioxo-1,3-dioxan-5-yl radicals;

Ra represents a hydrogen atom or an alkyl radical;

Rb represents a hydrogen atom or an alkyl radical;

Rc represents an alkyl or 5-tetrazolyl radical, a phenylalkyl radical in which the phenyl ring may be substituted with one or more substituents selected from halogen atoms and alkyl, alkoxy and alkylthio radicals or a phenyl radical which may be substituted with one or more substituents selected from halogen atoms and alkyl, alkoxy and alkylthio radicals;

or Rb and Rc form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals;

Rd represents an alkyl radical;

Re represents a hydrogen atom or an alkyl radical;

Rf represents an alkyl, cycloalkyl or cycloalkylalkyl radical;

or Re and Rf form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals;

Rg represents an alkyl, cycloalkyl or trifluoromethyl radical, or a phenyl radical which may be substituted with one or more substituents selected from cyano, alkoxy, nitro and amino radicals and halogen atoms;

Rh represents a 5-tetrazolyl radical;

Ri represents C=O or S=O;

Rj represents O or C=O;

n is equal to 0 or 1;

X represents a hydrogen atom or an alkyl or phenylalkyl radical;

alk represents an alkyl or alkylene radical;

alk' represents a hydroxyalkyl, hydroxyalkylene, alkoxyalkyl or alkoxyalkylene radical;

it being understood that the alkyl, alkylene and alkoxy radicals and portions of radicals contain 1 to 4 carbon atoms in a straight or branched chain and the cycloalkyl radicals or portions of radicals contain 3 to 6 carbon atoms;

an isomer of a compound of formula (I) or a salt of a compound of formula (I).

2. A compound of formula (I) according to claim 1 for which Rb and Rc form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals.

3. A compound of formula (I) according to claim 1 for which Re and Rf form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals.

4. A compound of formula (I) according to claim 1 for which:

$R_1$ represents a —$(CH_2)_n$—COORa or —$(CH_2)_n$—CONRbRc radical;

$R_2$ represents a phenyl radical which may be substituted with one or more substituents selected from halogen atoms and alkyl, alkoxy, hydroxyl, alkoxycarbonyl, trifluoromethyl and trifluoromethoxy radicals;

$R_3$ represents a —COORd or —CONReRf radical;

$R_4$ represents a hydrogen atom or an alkyl radical having one or two carbon atoms;

$R_5$ represents a phenyl radical which may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH═CH—COOX, —CO—COOX, —alk—SO₃H in salt form, —CH═CH—alk', —C(═NOH)—COOX, —S—alk—COOX, —SO—alk—COOX, —SO₂—alk—COOX, —O—CH₂—alk'—COOX, —CX═N—O—alk—COOX, —alk—N(OH)—CO—alk and —alk—SO₂H radicals;

Ra represents a hydrogen atom or an alkyl radical;

Rb represents a hydrogen atom or an alkyl radical;

Rc represents an alkyl or 5-tetrazolyl radical, a phenylalkyl radical in which the phenyl ring may be substituted with one or more substituents selected from halogen atoms and alkyl, alkoxy and alkylthio radicals or a phenyl radical which may be substituted with one or more substituents selected from halogen atoms and alkyl, alkoxy and alkylthio radicals;

or Rb and Rc form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals;

Rd represents an alkyl radical;

Re represents a hydrogen atom or an alkyl radical;

Rf represents an alkyl, cycloalkyl or cycloalkylalkyl radical;

or Re and Rf form, together with the nitrogen atom to which they are attached, a saturated or unsaturated mono- or polycyclic heterocycle containing 4 to 9 carbon atoms and one or more hetero atoms selected from oxygen, nitrogen and sulphur, and which may be substituted with one or more alkyl radicals;

n is equal to 0 or 1;

X represents a hydrogen atom or an alkyl or phenylalkyl radical;

alk represents an alkyl or alkylene radical;

alk' represents a hydroxyalkyl, hydroxyalkylene, alkoxyalkyl or alkoxyalkylene radical;

it being understood that the alkyl, alkylene and alkoxy radicals and portions of radicals contain 1 to 4 carbon atoms in a straight or branched chain and the cycloalkyl radicals or portions of radicals contain 3 to 6 carbon atoms; or an isomer or a salt of a compound of formula (I).

5. A compound selected from:

tert-butyl (2S,4S,5R)-5-methoxycarbonyl-3-{2-[3-(3-methylphenyl)ureido]acetyl}-4-phenyl-2-thiazolidinecarboxylate, 3-{3-[2-((2S,4S,5R)-2-tert-butoxycarbonyl-5-carboxy-4-phenyl-3-thiazolidinyl)-2-oxoethyl]ureido}phenylacetic acid, (S)-2-{3-{3-[2-((2S,4S,5R)-2-tert-butoxycarbonyl-5-carboxy-4-phenyl-3-thiazolidinyl)-2-oxoethyl]ureido}phenyl}propionic acid, tert-butyl (2S,4S,5R)-5-methoxycarbonyl-3-{2-[3-(3-methylphenyl)ureido]-acetyl}-4-(2-fluorophenyl)-2-thiazolidinecarboxylate, (2S,4S,5R)-2-tert-butoxycarbonyl-3-{2-[3-(3-methylphenyl)ureido]acetyl}-4-(2-fluorophenyl)-5-thiazolidinecarboxylic acid, or a salt of one of said compounds.

6. A process for preparing a compound of formula (I) according to claim 1 for which $R_1$ represents a —$(CH_2)n$—COORa radical, n is equal to 0 or 1, Ra represents an alkyl radical and $R_5$ represents a phenyl radical which may be substituted with one or more substituents selected from halogen atoms and alkyl, alkoxy, alkylthio, trifluoromethyl, alkoxycarbonyl, nitro, acyl, cyano, sulphamoyl, carbamoyl, alkoxyiminoalkyl, alkoxyaminocarbonyl, trifluoromethylsulphonamido, —alk—O—CO—alk, —alk—COOX, —alk—O—alk, —alk'—COOX, —O—alk—COOX, —CH═CH—COOX, —CO—COOX, —alk—SO₃H in salt form, —CH═CH—alk', —S—alk—COOX, —SO—alk—COOX, —SO₂—alk—COOX, —O—CH₂—alk'—COOX and —CX═N—O—alk—COOX radicals in which X is an alkyl or phenylalkyl radical, said process comprising the steps of reacting a derivative of formula:

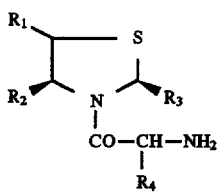

(II)

in which $R_1$ represents a —$(CH_2)n$—COORa radical, n is equal to 0 or 1, Ra represents an alkyl radical, and $R_2$, $R_3$ and $R_4$ have the same meanings as recited in claim 1, with a phenyl isocyanate in which the phenyl ring may be substituted with one or more substituents selected from halogen atoms and alkyl, alkoxy, alkylthio, trifluoromethyl, alkoxycarbonyl, nitro, acyl, cyano, sulphamoyl, carbamoyl, alkoxyiminoalkyl, alkoxyaminocarbonyl, trifluoromethylsulphonamido, —alk—O—CO—alk, —alk—COOX, —alk—O—alk, —alk'—COOX, —O—alk—COOX, —CH=CH—COOX, —CO—COOX, —alk—$SO_3H$ in salt form, —CH=CH—alk', —S—alk—COOX, —SO—alk—COOX, —$SO_2$—alk—COOX, —O—$CH_2$—alk'—COOX and —CX=N—O—alk—COOX radicals in which X is an alkyl or phenylalkyl radical, alk represents an alkyl or alkylene radical, and alk' represents a hydroxyalkyl, hydroxyalkylene, alkoxyalkyl or alkoxyalkylene radical;

isolating the product of said reaction; and optionally converting said isolated product into a salt.

7. A process for preparing a compound of formula (I) according to claim 1 for which $R_1$ represents a —$(CH_2)_n$—COORa radical, n is equal to 0 or 1 and Ra is an alkyl radical, said process comprising the steps of reacting a derivative of carbamic acid, which may be obtained in situ by the action of a derivative of carbonic acid selected from N,N'-carbonyldiimidazole, phosgene, diphosgene, triphosgene and p-nitrophenyl chloroformate on a derivative of formula:

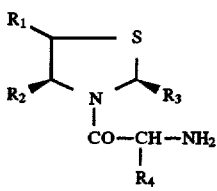

(II)

in which $R_1$ represents a —$(CH_2)_n$—COORa radical, Ra represents an alkyl radical, and $R_2$, $R_3$ and $R_4$ have the same meanings as recited in claim 1, with an aniline in which the phenyl ring which may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—$SO_3H$ in salt form, —CH=CH—alk', —C(=NOH)—COOX, —S—alk—COOX, —SO—alk—COOX, —$SO_2$—alk—COOX, —O—$CH_2$—alk'—COOX, —CX=N—O—alk—COOX, —alk—N(OH)—CO—alk, —alk—$SO_2H$, —$SO_2$—NH—CO—Rg, —$SO_2$—NH—$SO_2$—Rg, —CO—NH—CO—Rg, —CO—NH—$SO_2$—Rg, —$B(OH)_2$, —$C(NH_2)$=NOH, —$SO_2$—NH—Rh, —CO—NH—Rh,

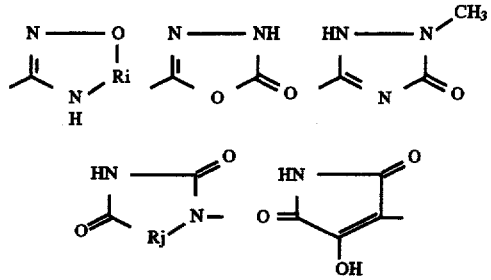

and 2,2-dimethyl-4,6-dioxo-1,3-dioxan-5-yl radicals; Ri represents C=O or S=O, Rj represents O or C=O, n is equal to 0 or 1, X represents a hydrogen atom or an alkyl or phenylalkyl radical, alk represents an alkyl or alkylene radical, and alk' represents a hydroxyalkyl, hydroxyalkylene, alkoxyalkyl or alkoxyalkylene radical;

isolating the product of said reaction; and optionally converting said isolated product into a salt.

8. A process for preparing a compound of formula (I) according to claim 1 for which $R_1$ represents a —$(CH_2)_n$—CONRbRc radical, said process comprising the steps of reacting a compound of formula (I) for which $R_1$ represents a —$(CH_2)_n$—COORa radical, n is equal to 0 or 1, and Ra represents a hydrogen atom, with an amine of formula HNRbRc in which Rb and Rc have the same meanings as recited in claim 1;

isolating the product of said reaction; and optionally converting said isolated product into a salt.

9. A process for preparing a compound of formula (I) according to claim 1 for which $R_1$ represents a —$(CH_2)_n$—COORa radical, n is equal to 0 or 1 and Ra represents a hydrogen atom, said process comprising the steps of hydrolysing a compound of formula (I), for which $R_1$ represents a —$(CH_2)_n$—COORa radical for which n is equal to 0 or 1 and Ra represents an alkyl radical;

isolating the product of said reaction; and optionally converting said isolated product into a salt.

10. A pharmaceutical composition comprising a pharmaceutically effective amount of at least one compound of formula (I) according to claim 1, together with a pharmaceutically acceptable carrier.

11. A compound of formula (I) according to claim 2, wherein said heterocycle is a morpholinyl residue, a thiomorpholinyl residue, a piperidyl residue which may be substituted with one or more alkyl radicals, a pyrrolidinyl residue, a 1,2,3,4-tetrahydroquinolyl residue or a alkylpiperazinyl residue.

12. A compound of formula (I) according to claim 3, wherein said heterocycle is a morpholinyl residue, a thiomorpholinyl residue, a piperidyl residue which may be substituted with one or more alkyl radicals, a pyrrolidinyl residue, a 1,2,3,4-tetrahydroquinolyl residue or a N-alkylpiperazinyl residue.

* * * * *

UNITED STATES PATENT AND TRADEMARK OFFICE
CERTIFICATE OF CORRECTION

PATENT NO. : 5,686,622
DATED : November 11, 1997
INVENTOR(S) : Marc CAPET et al.

It is certified that error appears in the above-identified patent and that said Letters Patent is hereby corrected as shown below:

On the Title Page, Item [57], in the Abstract, in the formula (I), "$R_6$" should read --$R_5$--.

Column 1, line 13, in the formula (I), "$R_6$" should read --$R_5$--.

Claim 1, column 25, line 53, in the formula (I), "$R_6$" should read --$R_5$--.

Signed and Sealed this

Twenty-first Day of July, 1998

Attest:

BRUCE LEHMAN

Attesting Officer

Commissioner of Patents and Trademarks